(12) United States Patent
Stilwell et al.

(10) Patent No.: US 9,744,266 B2
(45) Date of Patent: *Aug. 29, 2017

(54) FLOWABLE MATRIX COMPOSITIONS AND METHODS

(71) Applicant: AlloSource, Centennial, CO (US)

(72) Inventors: Reginald L. Stilwell, Parker, CO (US); Adrian C. Samaniego, Parker, CO (US); Brent Atkinson, Highlands Ranch, CO (US)

(73) Assignee: AlloSource, Centennial, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/858,295

(22) Filed: Sep. 18, 2015

(65) Prior Publication Data
US 2016/0008515 A1  Jan. 14, 2016

Related U.S. Application Data

(63) Continuation of application No. 13/712,295, filed on Dec. 12, 2012, now Pat. No. 9,162,011.

(60) Provisional application No. 61/577,299, filed on Dec. 19, 2011.

(51) Int. Cl.
| A61K 35/32 | (2015.01) |
| A61L 27/36 | (2006.01) |
| A61L 27/38 | (2006.01) |
| A61K 35/28 | (2015.01) |
| A61K 35/36 | (2015.01) |
| A61K 35/38 | (2015.01) |
| A61K 35/50 | (2015.01) |
| A61K 35/51 | (2015.01) |

(52) U.S. Cl.
CPC .......... *A61L 27/3691* (2013.01); *A61K 35/28* (2013.01); *A61K 35/32* (2013.01); *A61K 35/36* (2013.01); *A61K 35/38* (2013.01); *A61K 35/50* (2013.01); *A61K 35/51* (2013.01); *A61L 27/36* (2013.01); *A61L 27/362* (2013.01); *A61L 27/3629* (2013.01); *A61L 27/3662* (2013.01); *A61L 27/38* (2013.01)

(58) Field of Classification Search
None
See application file for complete search history.

(56) References Cited

U.S. PATENT DOCUMENTS

| 4,361,552 A | 11/1982 | Baur |
| 4,642,120 A | 2/1987 | Nevo et al. |
| 4,801,299 A | 1/1989 | Brendel et al. |
| 5,073,373 A | 12/1991 | O'Leary et al. |
| 5,290,558 A | 3/1994 | O'Leary et al. |
| 5,314,476 A | 5/1994 | Prewett et al. |
| 5,336,616 A | 8/1994 | Livesey et al. |
| 5,405,390 A | 4/1995 | O'Leary et al. |
| 5,439,684 A | 8/1995 | Prewett et al. |
| 5,507,813 A | 4/1996 | Dowd et al. |
| 5,510,396 A | 4/1996 | Prewett et al. |
| 5,531,791 A | 7/1996 | Wolfinbarger |
| 5,702,715 A | 12/1997 | Nikolaychik et al. |
| 5,723,010 A | 3/1998 | Yui et al. |
| 5,788,941 A | 8/1998 | Dalmasso et al. |
| 5,837,278 A | 11/1998 | Geistlich et al. |
| 5,876,451 A | 3/1999 | Yui et al. |
| 5,989,498 A | 11/1999 | Odland |
| 5,993,844 A | 11/1999 | Abraham et al. |
| 6,063,094 A | 5/2000 | Rosenberg |
| 6,152,142 A | 11/2000 | Tseng |
| 6,180,606 B1 | 1/2001 | Chen et al. |
| 6,203,755 B1 | 3/2001 | Odland |
| 6,326,019 B1 | 12/2001 | Tseng |
| 6,340,477 B1 | 1/2002 | Anderson |
| 6,432,710 B1 | 8/2002 | Boss |
| 6,576,015 B2 | 6/2003 | Geistlich et al. |
| 6,576,265 B1 | 6/2003 | Spievack |
| 6,616,698 B2 | 9/2003 | Scarborough |
| 6,652,594 B2 | 11/2003 | Francis et al. |
| 6,685,626 B2 | 2/2004 | Wironen |
| 6,777,231 B1 | 8/2004 | Katz |
| 6,830,149 B2 | 12/2004 | Merboth et al. |
| 6,849,273 B2 | 2/2005 | Spievack |
| 6,911,212 B2 | 6/2005 | Gertzman et al. |

(Continued)

FOREIGN PATENT DOCUMENTS

| WO | 2012083021 A1 | 6/2012 |
| WO | 2012083023 A1 | 6/2012 |
| WO | 2012088396 A2 | 6/2012 |
| WO | 2012112410 | 8/2012 |
| WO | 2012112417 | 8/2012 |
| WO | 2012112441 | 8/2012 |
| WO | 2012116372 A1 | 8/2012 |
| WO | 2012136701 A1 | 10/2012 |
| WO | 2012170905 A1 | 12/2012 |
| WO | 2013032938 A1 | 3/2013 |
| WO | 2013096214 A1 | 6/2013 |
| WO | 2014151091 A2 | 9/2014 |

OTHER PUBLICATIONS

Baheti, et al. "Excipients used in lyophilization of small molecules," Department of Pharmaceutical Technology, May 7, 2010, 15 pages.

(Continued)

*Primary Examiner* — Thane Underdahl
*Assistant Examiner* — Yvonne Pyla
(74) *Attorney, Agent, or Firm* — Kilpatrick Townsend & Stockton, LLP

(57) ABSTRACT

Flowable matrix compositions and methods of their use and manufacture are provided. Exemplary compositions may include a flowable, syringeable, putty-like form of acellular human dermal matrix. In some cases, compositions may include a moldable acellular collagen extracellular matrix. In use, the matrix compositions can be used to fill or treat skin voids, channel wounds, and other soft tissue deficiencies.

68 Claims, 8 Drawing Sheets

(56) References Cited

U.S. PATENT DOCUMENTS

| | | |
|---|---|---|
| 6,933,326 B1 | 8/2005 | Griffey et al. |
| 7,067,123 B2 | 6/2006 | Gomes et al. |
| 7,144,588 B2 | 12/2006 | Oray et al. |
| 7,172,629 B2 | 2/2007 | McKay |
| 7,316,822 B2 | 1/2008 | Binette et al. |
| 7,335,381 B2 | 2/2008 | Malinin |
| 7,347,876 B2 | 3/2008 | Tsai |
| 7,358,284 B2 | 4/2008 | Griffey et al. |
| 7,393,437 B2 | 7/2008 | Chan |
| 7,468,242 B2 | 12/2008 | Bellomo et al. |
| 7,494,802 B2 | 2/2009 | Tseng |
| 7,498,040 B2 | 3/2009 | Masinaei et al. |
| 7,498,041 B2 | 3/2009 | Masinaei et al. |
| 7,582,309 B2 | 9/2009 | Rosenberg et al. |
| 7,595,377 B2 | 9/2009 | Stone |
| 7,621,963 B2 | 11/2009 | Simon et al. |
| 7,625,581 B2 | 12/2009 | Laredo et al. |
| RE41,286 E | 4/2010 | Atkinson et al. |
| 7,723,108 B2 | 5/2010 | Truncale et al. |
| 7,727,550 B2 | 6/2010 | Siegal et al. |
| 7,754,232 B2 | 7/2010 | Fisher et al. |
| 7,807,458 B2 | 10/2010 | Schiller |
| 7,824,671 B2 | 11/2010 | Binder |
| 7,824,711 B2 | 11/2010 | Kizer et al. |
| 7,842,300 B2 | 11/2010 | Atkinson et al. |
| 7,875,296 B2 | 1/2011 | Binette et al. |
| RE42,208 E | 3/2011 | Truncale et al. |
| 7,902,145 B2 | 3/2011 | Chu |
| 7,914,779 B2 | 3/2011 | Hariri |
| 7,927,414 B2 | 4/2011 | Yang et al. |
| 7,928,280 B2 | 4/2011 | Hariri et al. |
| 7,977,094 B2 | 7/2011 | Masinaei et al. |
| 7,993,679 B2 | 8/2011 | Ingram et al. |
| 8,002,813 B2 | 8/2011 | Scarborough et al. |
| 8,021,692 B2 | 9/2011 | Hiles |
| 8,025,896 B2 | 9/2011 | Malaviya et al. |
| 8,039,016 B2 | 10/2011 | Drapeau et al. |
| 8,058,066 B2 | 11/2011 | Marshall |
| 8,071,135 B2 | 12/2011 | Liu et al. |
| 8,105,634 B2 | 1/2012 | Liu et al. |
| RE43,258 E | 3/2012 | Truncale et al. |
| 8,137,702 B2 | 3/2012 | Binette et al. |
| 8,142,502 B2 | 3/2012 | Stone et al. |
| 8,153,162 B2 | 4/2012 | Tseng |
| 8,158,141 B2 | 4/2012 | Chen |
| 8,163,549 B2 | 4/2012 | Yao et al. |
| 8,182,840 B2 | 5/2012 | Tseng |
| 8,182,841 B2 | 5/2012 | Tseng |
| 8,187,639 B2 | 5/2012 | Tseng |
| 8,198,245 B2 | 6/2012 | Niklason |
| 8,202,539 B2 | 6/2012 | Behnam et al. |
| 8,231,908 B2 | 7/2012 | Kinoshita |
| 8,309,106 B2 | 11/2012 | Masinaei et al. |
| 8,318,212 B2 | 11/2012 | Malinin |
| 8,323,701 B2 | 12/2012 | Daniel et al. |
| 8,357,403 B2 | 1/2013 | Daniel et al. |
| 8,372,437 B2 | 2/2013 | Daniel |
| 8,372,438 B2 | 2/2013 | Daniel et al. |
| 8,372,439 B2 | 2/2013 | Daniel et al. |
| 8,399,010 B2 | 3/2013 | McKay |
| 8,409,626 B2 | 4/2013 | Daniel |
| 8,420,126 B2 | 4/2013 | Tseng |
| 8,435,566 B2 | 5/2013 | Behnam et al. |
| 8,440,235 B2 | 5/2013 | Tseng |
| 8,455,009 B2 | 6/2013 | Tseng et al. |
| 8,460,714 B2 | 6/2013 | Tseng et al. |
| 8,496,970 B2 | 7/2013 | Binette et al. |
| 8,563,040 B2 | 10/2013 | Marchosky |
| 8,641,775 B2 | 2/2014 | Harmon et al. |
| 8,642,092 B2 | 2/2014 | Daniel et al. |
| 8,652,458 B2 | 2/2014 | Jackson et al. |
| 8,703,206 B2 | 4/2014 | Daniel et al. |
| 8,703,207 B2 | 4/2014 | Daniel et al. |
| 8,709,493 B2 | 4/2014 | Daniel et al. |
| 8,709,494 B2 | 4/2014 | Daniel |
| 8,822,415 B2 | 9/2014 | Trumpower et al. |
| 8,834,928 B1 | 9/2014 | Truncale et al. |
| 8,859,007 B2 | 10/2014 | Carter et al. |
| 8,883,210 B1 | 11/2014 | Truncale et al. |
| 9,084,767 B2 | 7/2015 | Daniel et al. |
| 9,162,011 B2 | 10/2015 | Stilwell et al. |
| 9,186,382 B2 | 11/2015 | Daniel et al. |
| 9,265,800 B2 | 2/2016 | Daniel |
| 9,265,801 B2 | 2/2016 | Daniel |
| 9,272,003 B2 | 3/2016 | Daniel et al. |
| 9,272,005 B2 | 3/2016 | Daniel |
| 2004/0048796 A1 | 3/2004 | Hariri |
| 2004/0059430 A1 | 3/2004 | Kim et al. |
| 2004/0260315 A1 | 12/2004 | Dell et al. |
| 2005/0019865 A1 | 1/2005 | Kihm |
| 2005/0058631 A1 | 3/2005 | Kihm |
| 2005/0159822 A1 | 7/2005 | Griffey et al. |
| 2005/0256588 A1 | 11/2005 | Sawa et al. |
| 2005/0288796 A1 | 12/2005 | Awad et al. |
| 2006/0210643 A1 | 9/2006 | Truncale et al. |
| 2006/0234376 A1 | 10/2006 | Mistry |
| 2007/0078522 A2* | 4/2007 | Griffey ............ A61K 9/0024 623/23.76 |
| 2007/0160588 A1 | 7/2007 | Kihm |
| 2007/0248575 A1 | 10/2007 | Connor et al. |
| 2008/0027542 A1 | 1/2008 | McQuillan et al. |
| 2008/0046095 A1 | 2/2008 | Daniel |
| 2008/0249638 A1 | 10/2008 | Asgari |
| 2009/0092674 A1 | 4/2009 | Ingram et al. |
| 2009/0253810 A1 | 10/2009 | Katz |
| 2009/0258082 A1 | 10/2009 | Nikaido et al. |
| 2010/0112543 A1 | 5/2010 | Ngo |
| 2010/0196333 A1 | 8/2010 | Gaskins et al. |
| 2010/0196478 A1 | 8/2010 | Masters |
| 2010/0291172 A1 | 11/2010 | Drunecky |
| 2010/0304487 A1 | 12/2010 | Truncale |
| 2011/0045044 A1 | 2/2011 | Masinaei et al. |
| 2011/0091434 A1 | 4/2011 | Miller |
| 2011/0104100 A1 | 5/2011 | Riordan |
| 2011/0151011 A1 | 6/2011 | Flynn |
| 2011/0160857 A1 | 6/2011 | Bracone |
| 2011/0206776 A1 | 8/2011 | Tom et al. |
| 2011/0238186 A1 | 9/2011 | Owens et al. |
| 2011/0256202 A1 | 10/2011 | Tom et al. |
| 2011/0262393 A1 | 10/2011 | Yang |
| 2011/0262516 A1 | 10/2011 | Zheng et al. |
| 2012/0009644 A1 | 1/2012 | Hamby et al. |
| 2012/0009679 A1 | 1/2012 | Hamby et al. |
| 2012/0010725 A1 | 1/2012 | Hamby et al. |
| 2012/0063997 A1 | 3/2012 | Hunter |
| 2012/0078378 A1 | 3/2012 | Daniel et al. |
| 2012/0082704 A1 | 4/2012 | Phillips et al. |
| 2012/0083900 A1 | 4/2012 | Samaniego et al. |
| 2012/0087958 A1 | 4/2012 | Dufrane et al. |
| 2012/0141595 A1 | 6/2012 | Tseng et al. |
| 2012/0142102 A1 | 6/2012 | Chen |
| 2012/0158134 A1 | 6/2012 | Codori-Hurff et al. |
| 2012/0164114 A1 | 6/2012 | Abbot |
| 2012/0189583 A1 | 7/2012 | Liu et al. |
| 2012/0189586 A1 | 7/2012 | Harrell |
| 2012/0191184 A1 | 7/2012 | Chen |
| 2012/0201787 A1 | 8/2012 | Abbot |
| 2012/0221118 A1 | 8/2012 | Bartee et al. |
| 2012/0225484 A1 | 9/2012 | Bhatia et al. |
| 2012/0263763 A1 | 10/2012 | Sun et al. |
| 2012/0269774 A1 | 10/2012 | Ichim |
| 2012/0276080 A1 | 11/2012 | Kinoshita et al. |
| 2012/0294810 A1 | 11/2012 | Daniel |
| 2012/0294811 A1 | 11/2012 | Daniel |
| 2012/0294908 A1 | 11/2012 | Daniel et al. |
| 2012/0294910 A1 | 11/2012 | Daniel et al. |
| 2012/0328690 A1 | 12/2012 | Tseng et al. |
| 2013/0004465 A1 | 1/2013 | Aberman |
| 2013/0006385 A1 | 1/2013 | Daniel |
| 2013/0052169 A1 | 2/2013 | Marom |
| 2013/0103061 A1 | 4/2013 | Harper |
| 2013/0108670 A1 | 5/2013 | Lynch et al. |
| 2013/0121970 A1 | 5/2013 | Owens et al. |
| 2013/0189338 A1 | 7/2013 | Drapeau et al. |

(56) References Cited

U.S. PATENT DOCUMENTS

| | | |
|---|---|---|
| 2013/0190893 A1 | 7/2013 | Roock et al. |
| 2013/0202676 A1 | 8/2013 | Koob et al. |
| 2013/0209572 A1 | 8/2013 | Wilhelmi et al. |
| 2013/0218274 A1 | 8/2013 | Spencer et al. |
| 2013/0230561 A1 | 9/2013 | Daniel et al. |
| 2013/0287741 A1 | 10/2013 | Stilwell et al. |
| 2013/0344162 A1 | 12/2013 | Morse et al. |
| 2014/0017280 A1 | 1/2014 | Daniel et al. |
| 2014/0037598 A1 | 2/2014 | Jansen et al. |
| 2014/0050788 A1 | 2/2014 | Daniel et al. |
| 2014/0052247 A1 | 2/2014 | Daniel et al. |
| 2014/0052274 A1 | 2/2014 | Koob et al. |
| 2014/0058527 A1 | 2/2014 | Truncale et al. |
| 2014/0106447 A1 | 4/2014 | Brown et al. |
| 2014/0112894 A1 | 4/2014 | Zheng et al. |
| 2014/0127177 A1 | 5/2014 | Tom et al. |
| 2014/0127317 A1 | 5/2014 | Jansen et al. |
| 2014/0140964 A1 | 5/2014 | Brown et al. |
| 2014/0140966 A1 | 5/2014 | Tom et al. |
| 2014/0205646 A1 | 7/2014 | Morse et al. |
| 2014/0212471 A1 | 7/2014 | Drapeau et al. |
| 2014/0212499 A1 | 7/2014 | Cooper et al. |
| 2014/0214176 A1 | 7/2014 | Daniel et al. |
| 2014/0222159 A1 | 8/2014 | Bursac et al. |
| 2014/0234387 A1 | 8/2014 | Daniel et al. |
| 2014/0255496 A1 | 9/2014 | Daniel et al. |
| 2014/0255506 A1 | 9/2014 | Behnam et al. |
| 2014/0255508 A1 | 9/2014 | Morse et al. |
| 2014/0294777 A1 | 10/2014 | Tom et al. |
| 2014/0301986 A1 | 10/2014 | Tom et al. |
| 2014/0302162 A1 | 10/2014 | Morse et al. |
| 2014/0314822 A1 | 10/2014 | Carter et al. |
| 2014/0343688 A1 | 11/2014 | Morse et al. |
| 2015/0004211 A1 | 1/2015 | Yoo et al. |
| 2015/0004247 A1 | 1/2015 | Carter et al. |
| 2015/0010506 A1 | 1/2015 | Jansen et al. |
| 2015/0010609 A1 | 1/2015 | Tom et al. |
| 2015/0010610 A1 | 1/2015 | Tom et al. |
| 2015/0017222 A1 | 1/2015 | Yoo et al. |
| 2015/0140057 A1 | 5/2015 | Yoo et al. |
| 2015/0140114 A1 | 5/2015 | Sasko |
| 2015/0174297 A1 | 6/2015 | Daniel |
| 2015/0209475 A1 | 7/2015 | Daniel |
| 2015/0265747 A1 | 9/2015 | Daniel |
| 2016/0008511 A1 | 1/2016 | Stilwell et al. |
| 2016/0008512 A1 | 1/2016 | Stilwell et al. |

OTHER PUBLICATIONS

Brigido, Stephen A., et al. "Use of an Acellular Flowable Dermal Replacement Scaffold on Lower Extremity Sinus Tract Wounds a Retrospective Series." Foot & Ankle Specialist 2.2 (2009): 7 pgs.

Carpenter, et al. "Rational Design of Stable Lyophilized Protein Formulations: Theory and Practice," Center for Pharmaceutical Biotechnology, University of Colorado, 2002, 25 pages.

Charulatha, et al. "Crosslinking density and resorption of dimethyl suberimidate-treated collagen," Department of Biophysics, Sep. 3, 1996, 9 pages.

Crapo, P. et al., "An overview of tissue and whole organ decellularization processes," Biomaterials 32(12):3233-3243 (2011).

Davis, et al. "Review: Regulation of Tissue Injury Reponses by the Exposure of Matricryptic Sites within Extracellular Matrix Molecules," American Journal of Pathology, vol. 156, No. 5, May 2005, 10 pages.

Gilbert, TW, et al. "Decellularization of tissues and organs." Biomaterials, 27, (2006), 1 pg. (Abstract Only).

Imamura, et al. "Effects of Types of Sugar on the Stabilization of Protein in the Dried State," Department of Bioscience and Biotechnology, Faculty of Engineering, Okayama University, Sep. 7, 2002, 9 pages.

International Search Report and Written Opinion of PCT/US12/70128 filed Dec. 17, 2012, dated Feb. 26, 2013, 26 pages.

Kendrick, et al. "Physical Stabilization of Proteins in Aqueous Solution," Kluwer Academic/Plenium Publishers, 2002, 19 pages.

Khan, et al."Use of Collagen as an implantable material in the reconstructive procedure—an overview," www.biolmedonline.com , 2011, 8 pages.

Landsman, A., et al. "Graftjacket Xpress: Flowable Soft-Tissue Scaffold Sales Brochure." 2011, 8 pgs.

Liu, et al. "Freeze-Drying of Proteins From a Sucrose-Glycine Excipient System: Effect of Formulation Composition on the Initial Recovery of Protein Activity," retrieved from http://aapspharmscitech.org Feb. 11, 2005, 8 pages.

Lu, et al., Journal of Biomechanical Engineering, Aug. 2008, vol. 130, pp. 041011-1 to 041011-10.

Nakagawa, et al. "In vivo measurement of the water content in the dermis by confocal Raman spectroscopy," Skin Research and Technology, 2010, 5 pages.

"Normal Saline Solution", Paramedicine, 2014, retrieved from the internet at: http://www.paramedicine.com/pmc/Normal_Saline_Solution.html.

Shermak, MA, et al. "Reconstruction of complex cranial wounds with demineralized bone matrix and bilayer artificial skin." J. Craniofac Surg., May 11, 2000, (3): 1 pg. (Abstract Only).

Strong, et al. "Freeze-Drying of Tissues," Musculoskeletal Tissue Banking, 1993 (WW Tomford ed.) Ravens Press, NY, 26 pages.

Venkatasubramanian, et al. " Effects of Freezing and Cryopreservation on the Mechanical Properties of Arteries," Annals of Biomedical Engineering, vol. 34, No. 5, May 2006, 10 pages.

Wilsteed, EM et al.; "An ultrastructural comparison of derma-epidermal separation techniques", J. Cutan. Pathol., 1991, (18), 1 pg. (Abstract Only).

Zeng, et al. "Effects of molecular weight of polyvinylpyrrolidone on the glass transition and crystallization of co-lyophilized sucrose," International Journal of Pharmaceutics, Jan. 31, 2001, 11 pages.

* cited by examiner

FLOWABLE MATRIX COMPOSITIONS AND METHODS

CROSS REFERENCE TO RELATED APPLICATION

This application is a continuation application of U.S. patent application Ser. No. 13/712,295, filed Dec. 2, 2012, which claims the benefit of the filing date of U.S. Prov. Patent Appl. No. 61/577,299, entitled "FLOWABLE MATRIX COMPOSITIONS AND METHODS," filed Dec. 19, 2011, the entire disclosures of which are incorporated herein by reference for all purposes.

BACKGROUND

Embodiments of the present invention are directed in general to the field of wound treatments, and in particular to flowable human tissue compositions, and methods of their use and manufacture.

Human tissue compositions, which may be derived from cadaveric donors, have been used for many years in various surgical procedures, including treatments for abrasions, lacerations, burns, and other wounds. Although human tissue compositions and methods are presently available and provide real benefits to patients in need thereof, many advances may still be made to provide improved dressing systems and methods for treating patients. The flowable matrix compositions and treatment and manufacture methods described herein provide further solutions and answers to these outstanding needs.

BRIEF SUMMARY

Embodiments of the present invention provide flowable matrix compositions and methods suitable for use in advanced wound management, including acute and chronic wound treatment, general surgery, plastic and reconstructive surgery, uro-gynecological surgery, and numerous surgical procedures where an irregular tissue defect repair may be beneficial.

An exemplary flowable matrix composition can be produced from a soft tissue, such as an allograft human dermis which has been recovered from a tissue donor. The tissue can be aseptically processed to remove cells, while preserving natural biologic components and structural features of the tissue. The soft tissue can be further processed to yield a putty-like, pliable, matrix. The flowable matrix can be supplied for surgical use as a sterile product. In some cases, the flowable matrix can be loaded in an applicator, such as a syringe. An applicator or syringe can be of any size or volume. For example, a 6 c.c. syringe may be used. In use, a surgeon or other medical personnel may deliver the flowable matrix to an irregularly shaped wound site of a patient. In some cases, a decellularized or partially decellularized matrix may be used for the repair or replacement of damaged or inadequate integumentary tissue. In some instances, the soft tissue matrix is prepared from a tissue containing an amount of water or hydration. In some cases, water may be added to the matrix during processing. In some cases, the preparation may be processed without the incorporation of additional water. In some cases, the matrix can be processed without removing water therefrom. In some instances, the soft tissue matrix composition is at least partially hydrated when packaged. The surgeon or medical professional may use the matrix composition directly upon opening the packaged product, without performing additional mixing or rehydration steps.

Flowable matrix embodiments of the present invention are well suited for a variety of therapeutic applications, including wound care and burn case. Exemplary wound care applications may involve treatment of chronic wounds, tunneling, channel, or invaginated wounds, wounds presenting a deep and irregular wound bed, and the like. The flowable, putty-like, compliant properties of the matrix render it particularly suitable for such indications. The flowable matrix or scaffold can be placed into the tunnels and tracts of chronic non-healing wounds which include, but are not limited to, venous leg ulcers and diabetic foot ulcers, acute wounds which include drained abscesses, and cysts. In some cases, the flowable matrix can be administered to a patient via a delivery cannula. In some cases, the flowable matrix can be delivered or syringed percutaneously through a large gauge needle to the patient. In some cases, the flowable matrix can be administered to a patient as part of a surgical procedure for treating a rotator cuff injury or tear.

In one aspect, embodiments of the present invention encompass methods for producing a soft tissue matrix composition for use in a patient treatment. Exemplary production methods may include obtaining a portion of soft tissue material, and processing the portion of soft tissue material according to a protocol which comprises cryofracturing the portion of soft tissue material. The processing protocol may provide the soft tissue matrix composition. In some instances, the soft tissue material is acellular. In some instances, the soft tissue material is at least partially decellularized. In some instances, the soft tissue material is not partially or completely decellularized. According to some embodiments, a processing protocol may include triturating the cryofractured soft tissue material. For example, a triturating step may include milling a cryofractured portion of soft tissue material. In some cases, a processing protocol may include adding a wetting agent to the triturated soft tissue material. In some cases, the wetting agent may include a saline solution. In some cases, the soft tissue matrix composition may have a putty consistency. In some cases, the portion of soft tissue material is in a naturally hydrated state prior to processing according to the protocol. In some cases, the portion of soft tissue material is in a partially hydrated state prior to processing according to the protocol. In some cases, the soft tissue material is non-immunogenic or has reduced immunogenicity. In some cases, the soft tissue material is reduced in cytotoxicity. In some cases, the soft tissue material includes epidermal tissue, a dermal tissue, a placental derived tissue, an amnion tissue, a chorionic tissue, a tendon tissue, an umbilical cord tissue, an intestine tissue, or a musculoskeletal non-osseous tissue. In some cases, the soft tissue material includes human soft tissue, an equine soft tissue, a bovine soft tissue, a porcine soft tissue, an ovine soft tissue, a caprine soft tissue, or an avian soft tissue. In some cases, the soft tissue material includes a human dermal tissue. In some cases, the cryofracturing step includes treating the portion of soft tissue material with liquid nitrogen. In some cases, the cryofracturing step includes treating the soft tissue material with liquid nitrogen for a period of about less than one hour. In some cases, the cryofracturing step includes treating the soft tissue material with liquid nitrogen for a period within a range from about 10 second to about 1 minute. In some cases, the cryofracturing step renders the portion of soft tissue material stiff and friable. According to some embodiments, methods may include combining the soft tissue material matrix composition with a biocompatible carrier, a thickener, an adhesive, or any mixture, combination, or sub-combination thereof. Some methods may include loading the soft tissue material matrix composition into an applicator assembly. According to some embodiments, an applicator assembly may include a syringe mechanism or a cannula mechanism. In some cases, the cryofracturing partially disrupts extracellular matrix tissue macro architecture within the soft tissue material. In some cases, the cryofracturing step partially disrupts extracellular matrix tissue macro architecture within the soft tissue material, and the triturating step further disrupts extracellular matrix tissue macro architecture within the soft tissue material. In some cases, the soft tissue material includes a delaminated dermal tissue. In some cases, the soft tissue material includes a non-delaminated dermal tissue. In some cases, methods may include combining the soft tissue matrix composition with a stromal volume fraction, a progenitor cell population, or a stem cell population.

In another aspect, embodiments of the present invention encompass methods for producing a soft tissue matrix composition for use in a patient treatment. Exemplary methods may include obtaining a portion of soft tissue material, and partially homogenizing the portion of soft tissue material so as to produce the soft tissue matrix composition.

In another aspect, embodiments of the present invention encompass soft tissue matrix compositions for use in a patient treatment. Exemplary compositions may include a soft tissue material having a mechanically disrupted macrostructure and a partially disrupted collagen microfibrillar architecture. In some cases, a soft tissue matrix composition may include a wetting agent. In some cases, the wetting agent may include a saline solution. In some cases, the composition is present in an applicator assembly. In some cases, the soft tissue material is acellular. In some cases, the soft tissue material is at least partially decellularized. In some cases, the soft tissue material is not partially or completely decellularized. In some cases, the soft tissue matrix composition does not adhere to a surgical glove material. In some cases, the surgical glove material comprises a member selected from the group consisting of latex, neoprene, vinyl, and Nitrile. In some cases, a matrix composition may also include a stromal volume fraction, a progenitor cell population, or a stem cell population.

In still a further aspect, embodiments of the present invention encompass methods for treating a soft tissue of a patient. Exemplary methods may include obtaining a soft tissue matrix composition, and administering the soft tissue matrix to the soft tissue of the patient. In some cases, the soft tissue material is acellular. In some cases, the soft tissue comprises a defect. In some cases, the soft tissue defect is a skin void, and an administering step includes at least partially filling the skin void with the soft tissue matrix composition. In some cases, an administering step includes delivering the soft tissue matrix with an applicator assembly to the soft tissue, and the applicator assembly includes a cannula mechanism or a syringe mechanism. In some cases, an administering step includes manually delivering the soft tissue matrix with a gloved hand. In some cases, the soft tissue defect is a skin void, a channel wound, an ulcer, a surgical wound, a trauma wound, a chronic wound, an acute wound, or an exsanguinating site. In some cases, the soft tissue defect is an ulcer wound such as a pressure ulcer, a venous ulcer, a diabetic ulcer, or a chronic vascular ulcer. In some cases, the soft tissue defect is a surgical wound such as a general surgery wound, a plastic surgery wound, a reconstructive surgery wound, a urological surgery wound, or a gynecological surgery wound. In some cases, methods may also include at least partially covering the matrix, the tissue, or both, with a wound dressing. In some cases, methods may also include forming the soft tissue matrix composition into a shape suitable for placement at or within the soft tissue. In some cases, the soft tissue defect is an exsanguinating site, and administration of the soft tissue matrix activates a hemostatic cascade at the exsanguinating site. In some cases, the soft tissue matrix composition also includes a stromal volume fraction, a progenitor cell population, or a stem cell population.

The above described and many other features and attendant advantages of embodiments of the present invention will become apparent and further understood by reference to the following detailed description when considered in conjunction with the accompanying drawings.

DETAILED DESCRIPTION

Figure 1:
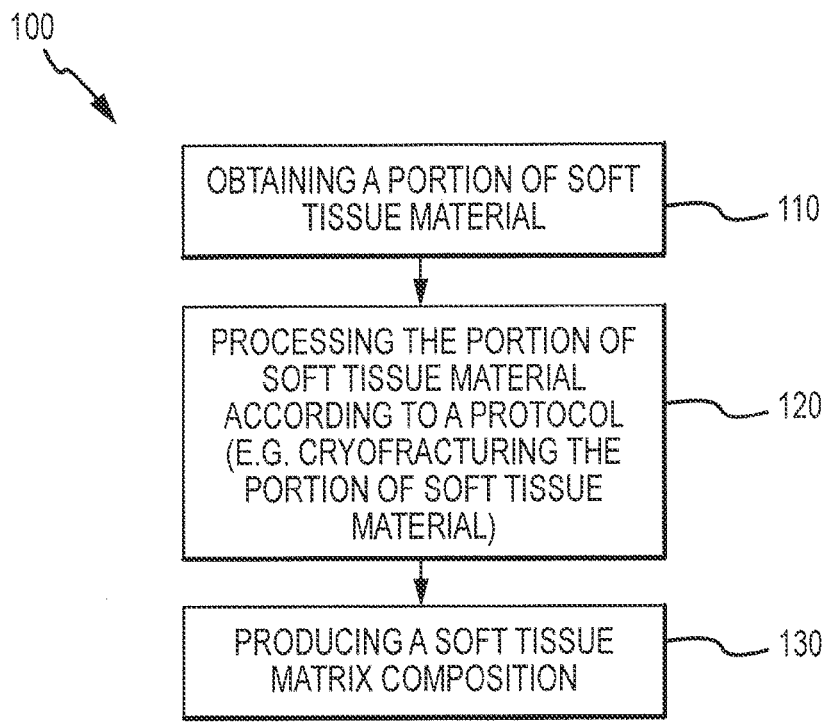
FIG. 1 illustrates aspects of a method for producing a soft tissue matrix composition according to embodiments of the present invention.

Embodiments of the present invention encompass flowable matrix compositions and methods. Exemplary compositions may include a flowable, putty-like form of acellular human dermal matrix that can be delivered from a syringe. In some cases, compositions may include a moldable acellular collagen extracellular matrix. In use, the matrix compositions can be used to fill or treat skin voids, channel wounds, and other soft tissue deficiencies.

Material composition embodiments of the invention may include an acellular human dermal matrix (e.g. a collagenous matrix derived from full-thickness or partial-thickness human skin that has been subjected to a gentle decellularization process) and a moistening solution such as normal saline, phosphate buffered saline, Lacted Ringers solution, or a similar physiological compatible moistening solution. In some cases, the material may include only the dermal matrix and the moistening solution.

According to some embodiments, a composition may include any suitable biocompatible extracellular matrix material derived from humans, animals, sources such as allograft material (human derived tissue), placental material, xenograft material including bovine, ovine, caprine, porcine, equine, avian, or other animal sourced tissue. In addition to these materials, matrix compositions may include any collagenous material capable of being delivered through a cannula. In addition to human tissue allograft compositions for transplantation, other materials as noted herein can be used, for transplantation and other therapeutic purposes.

Flowable matrix compositions, such as a human collagenous matrix, can be used in the surgical fields, for example where it may be desirable to fill or treat an acute incisional defect or chronic wound with the matrix for the purpose of allowing cellular infiltration and angiogenesis to occur in order to affect a post-surgical healing response. In some cases, a primary medical indications for use may include the management of wounds or conditions, including without limitation partial and full-thickness wounds, pressure ulcers, venous ulcers, diabetic ulcers, chronic vascular ulcers, tunneled/undermined wounds, surgical wounds, donor sites/grafts, post-Mohs surgery, post laser surgery, podiatric, wound dehiscence, and trauma wounds such as abrasions, lacerations, second-degree burns, and skin tears. In some embodiments, a matrix composition may be intended for a one-time use.

Relatedly, flowable matrix compositions may be use in the therapeutic intervention of chronic and acute wounds. In some cases, matrix compositions may permit or facilitate the in situ delivery of a hemostatic material to an exsanguinating site. In some cases, a flowable matrix composition may provide a vehicle for the delivery of collagen, as a hemostatic material, to hard to reach bleeding sites. The collagen can operate to activate the hemostatic cascade by the mechanism of platelet aggregation. Subsequent to platelet adhesion and aggregation initiated by collagen, the hemostatic effect of fibrinogen being activated to form a fibrin clot ensues thereby forming a clot and diminishing or stopping the flow of blood from the injured site.

In clinical applications, matrix compositions can be used for soft tissue integumental repair. For example, a putty-like, moldable acellular dermal matrix can be delivered through a cannula or other syringe attachment to a treatment site. In some cases, matrix compositions can be used to deliver a hemostatic material (e.g. collagen) to a bleeding site. Matrix compositions can be used to treat channeling wounds, deep full-thickness integumental defects, and other wounds or conditions where a putty-like, moldable matrix is suitable for application. In some case, matrix compositions provide a beneficial therapeutic use for achieving hemostasis at a bleeding site.

Embodiments of the present invention encompass matrix compositions which can be molded or otherwise handled by a gloved hand without sticking to the glove. Relatedly, exemplary matrix compositions can be used without sticking to operative instruments which may come into contact with the matrix. Hence, matrix compositions can be easily applied with a gloved hand without sticking to the gloves or other surfaces.

According to some embodiments, matrix compositions can be applied to a soft tissue defect such as a channeling wound in similar fashion to a "putty-like" material wherein a medical practitioner may mold a portion of the matrix composition into an irregularly shaped soft tissue void with a gloved finger. In some cases, a syringe equipped with a standard medical cannula of appropriate length can be used to deliver the matrix composition to a treatment site. Relatedly, in some cases a matrix composition can be supplied in pre-loaded syringe assembly. Optionally, a surgeon or practitioner may use the syringe and cannula as a directed delivery device whereby the matrix composition is delivered to an irregular or channel wound site or other soft tissue defect.

Matrix compositions can be applied to a patient or individual so as to fill irregular wounds or soft tissue defects in a complete fashion, which may otherwise be difficult to treat with rigid flat or rectangular devices. By providing a flowable material which completely contacts a wound bed, improvement in healing can be realized. Such enhanced or complete contact with the wound bed promotes proper revascularization, angiogenesis, and wound healing. Matrix compositions are particularly well suited for use in treating an irregularly shaped wound bed, due to the enhanced contact between the matrix and the wound.

According to some embodiments, a full-thickness human skin can be treated to remove the epidermal layer, and optionally further treated to at least partially remove the cellular contents and nucleic detritus. The resultant human dermal matrix, optionally in acellular form or at least partially in acellular form, can then be treated by a cryofracturing technique to render it stiff and friable. The friable matrix can then be triturated, for example by milling. The resultant composition matrix material can provide a putty-like consistency, optionally upon thawing. In some cases, the matrix composition is not in a powder form, and hence is not as susceptible to the build up of static electrical charges. According to some embodiments, the soft tissue matrix composition is provided to the surgeon or administered to the patient in a native form, without the presence of other materials or additives.

In some cases, a matrix composition, such as a flowable collagenous matrix material, may include various biocompatible carriers, thickeners, or adhesives, including but not limited to carboxymethylcellulose, poloxymer, and fibrin sealant. Likewise, the friable matrix can be triturated by any of a variety of triturative methodologies, such as partial homogenization of a non-cryotreated acellular matrix and variations thereof. Such triturations can be performed so as to provide particular matrix particle sizes, in some instances.

Turning now to the drawings, FIG. 1 illustrates a method of producing a soft tissue matrix composition for use in a patient treatment, according to embodiments of the present invention. Manufacturing method 100 includes obtaining a portion of soft tissue material, as shown by step 110, processing the portion of soft tissue material according to a protocol which includes cryofracturing the portion of soft tissue material, as shown by step 120. The processing protocol provides the soft tissue matrix composition, as shown by step 130. In some cases, the soft tissue material is acellular, or at least partially acellular. For example, the soft tissue material may be processed according to a decellularization treatment to remove some or all of the cellular components therefrom. Decellularization may be accomplished by known techniques such as those referenced in Gilbert, T W, Sellaro, T L and Badylak, S F; "Decellularization of tissues and organs", Biomaterials, 27, (2006), 3675-3683, the content of which is incorporated herein by reference. Embodiments of the present invention also encompass tissue which are processed according to decellularization techniques such as those described in U.S. Pat. No. 5,336,616, the content of which is incorporated herein by reference. In some cases, the processing protocol of step 120 includes triturating the cryofractured soft tissue material. Optionally, the protocol of step 120 may include adding a wetting agent to the triturated soft tissue material. In some cases, the wetting agent includes a saline solution. In some cases, a wetting agent may include any of the known surface active amphiphilic chemicals that typically act to lower the surface tension of aqueous solvents and are capable of forming micelles. Such wetting agents may be any of the surfactants known in the field as anionic, cationic or nonionic surfactants. A nonexhaustive list of specific wetting agents includes phosphate buffered saline (PBS), sodium dodecyl sulfate, sodium stearate, benzalkonium chloride, 3-[(3-cholamidopropyl)dimethylammonio]-1-propanesulfonate (CHAPS), lecithin, Triton X-100 ((p-t-Octylphenoxy) polyethoxyethanol), and Nonoxynol-9. According to exemplary embodiments of the present invention, the soft tissue matrix composition has a putty consistency or viscosity. Relatedly, the soft tissue matrix composition may have a shear resistance force within a range from about 250 Pascal seconds (Pa s) to about 2500 Pascal seconds. In some cases, the soft tissue matrix composition has a shear resistance force within a range from about 1000 Pascal seconds to about 2000 Pascal seconds. Such shear resistance forces or consistencies can be measured by standard viscometric or rheometric methods, including without limitation Brookfield viscometers, Stormer viscometers, ICI Cone and Plate viscometers, rheometers, and the like. In some instances, the shear resistance or flowability of the matrix composition can be modified by adjusting an amount of wetting agent added to the triturated soft tissue material. In some cases, a matrix composition can be produced without including a wetting agent. Such matrix compositions may present a more putty-like consistency (e.g. higher viscosity), as compared with matrix compositions which include a wetting agent (e.g. lower viscosity). The amount of wetting agent may determine which types of application processes can be used to administer the composition. For example, a highly flowable matrix composition containing a larger amount of wetting agent may be suitable for delivery by a syringe, and a less flowable matrix composition containing little or no wetting agent may be suitable for manual delivery as a molded or formed plug or filling. In some cases, a plug can be manually formed. In some cases, a plug can be mechanically formed, for example with a press mechanism. Optionally, a plug can be molded into a desired shape using both manual and mechanical forming techniques. In some cases, a plug can be formed so that it provides a shape or surface that is complimentary to a shape or surface of a patient wound. For example, for treating a patient wound presenting a cylindrical channel feature, the plug can be formed into a shape presenting a complimentary tubular feature which is configured for placement in the patient wound channel feature.

In some cases, an exemplary flowable matrix preparation may be deliverable or flowable through an 18 g needle (1.27 mm; 0.050 inches) but not a 26 g needle (0.4636 mm; 0.01825 inches).

According to some embodiments, the portion of soft tissue material may be in a naturally hydrated state prior to processing according to the protocol of step 120. In some instances, the portion of soft tissue material may be in a partially hydrated state prior to processing according to the protocol of step 120. In some instances, the processing protocol of step 120 may include triturating a cryofractured soft tissue material. Trituration may be accomplished by blending or milling techniques, for example. In some instances, a blender, mill, or other trituration process may be selected or performed so as to provide matrix particles of various sizes. Relatedly, different administration techniques may involve the delivery of different particle sizes. For example, the particle size of the of the matrix can be increased or decreased to allow the product to be delivered through a cannula (e.g. larger particles) or through a needle (e.g. smaller particles), respectively.

According to some embodiments, the matrix composition presents a consistency or degree of flowability, such that it can be easily dispensed or extruded through syringe opening (e.g., 3 mm orifice) or a catheter or tube (e.g. inner diameter less than 4 mm) upon application of a standard amount of syringe pressure which may be applied manually in the surgical setting.

In some cases, the soft tissue material or matrix composition is non-immunogenic, or has reduced immunogenicity in comparison to a tissue material which has not been processed according to embodiments described herein. For example, the material or composition may elicit no immune response, or a limited immune response, when introduced into a patient. In some cases, the soft tissue material or matrix composition is non-cytotoxic, or has reduced cytotoxicity in comparison with a tissue material which has not been processed according to embodiments described herein. Techniques for the decellularization processes may entail the use of detergents, surfactants, acids, bases, salts, and other chemical entities which result in the presence of detectable residual chemicals in the acellular tissue matrix. According to some embodiments, it may be desirable to sufficiently remove these residuals, which may otherwise in some cases exhibit a cytotoxic response if they still remain in certain amounts following decellularization. In this way, removal of the residuals can reduce the possibility of a cytotoxic response. In some cases, such cytotoxicity may prevent, stop, or otherwise inhibit successful incorporation of the matrix into the implanted host. Therefore it may be desirable to remove as much of any residual decellularizing process chemicals as possible. According to some embodiments, the trituration or comminution of the tissue followed by successive washing steps can maximize the surface area of the tissue particles that are exposed to the washing solution, thereby significantly reducing the presence of any potential residual process chemicals. This significant reduction of residuals will minimize or prevent a potentially cytotoxic response of the final matrix product. Such washing agents may include any of the several solvents that are miscible with a hydrated medium and may exhibit hydrophobic or hydrophilic solvation characteristics depending upon the decellularization agent used and may be exemplified by sterile water, sterile physiological saline, sterile phosphate buffered saline, or any number of mixtures of these with organic solvents such as 1-propanol, 2-propanol, acetone, methanol or similar minimally polar solvents.

Soft tissue material, such as the material obtained in step 110, may include an epidermal tissue, a dermal tissue (e.g. full-thickness or partial-thickness), a placental derived tissue, an amnion tissue, a chorionic tissue, a tendon tissue, an umbilical cord tissue, an intestine tissue, a musculoskeletal non-osseous tissue, or the like. In some cases, soft tissue material may include a human soft tissue, an equine soft tissue, a bovine soft tissue, a porcine soft tissue, an ovine soft tissue, a caprine soft tissue, an avian soft tissue, or the like. According to exemplary embodiments, the soft tissue material includes a human dermal tissue. For example, the soft tissue material may include full-thickness or partial-thickness human skin. In some cases, soft tissue material may include a cartilage tissue or a muscle tissue.

The processing protocol illustrated in step 120 may include subjecting the tissue material to a cryofracturing technique. For example, step 120 may include treating the portion of soft tissue material with liquid nitrogen. In some cases, a cryofracturing step may include treating the soft tissue material with liquid nitrogen for a period of about less than one hour. In some cases, the cryofracturing step may include treating the soft tissue material with liquid nitrogen for a period within a range from about 10 second to about 1 minute. According to exemplary embodiments, the cryofracturing step may render the portion of soft tissue material stiff and friable. For example, cryofracturing processes, which may include immersion in liquid nitrogen that applied to a soft tissue material can render it suitably friable for subsequent trituration. A soft tissue material matrix composition, such as that obtained in step 130, may be combined with a biocompatible carrier, a thickener, or an adhesive. Exemplary carriers or thickeners may include any of the Generally Recognized as Safe (GRAS) excipients such as carboxy methyl cellulose (CMC), methylcellulose, agar, carrageenan, modified starch, pectin, poloximers or similar materials. Optionally, adhesives such as fibrin glue may be employed. Such fibrin glue can be derived from recombinant human fibrin combined with human or bovine derived thrombin. A soft tissue matrix composition may also be loaded into an applicator assembly, for subsequent use by a surgeon or other medical personnel. In some cases, an applicator assembly may include a syringe mechanism and a cannula mechanism.

The processing protocol of step 120 may include cryofracturing the soft tissue material so as to at least partially physically disrupt extracellular matrix collagen or tissue macro architecture within the soft tissue material. In some cases, as further discussed elsewhere herein, a cryofracturing process may partially disrupt extracellular matrix collagen or tissue macro architecture within the soft tissue material, and a subsequent triturating process may further disrupt extracellular matrix collagen bundles within the soft tissue material.

Either or both of the cryofracturing and triturating processes may be applied to any of a variety of tissue types, including without limitation amnion tissue, umbilical cord tissue, intestine tissue, or other soft tissues. Any of these tissues may be similarly treated either with or without a prior decellularization treatment. Hence, for example, skin, amnion, tendon, or other tissues can be cryofractured and rendered into a putty-like medium. In some embodiments, such tissues may be rendered non-immunogenic prior to manufacturing them into a putty, for example if the end use is implantation within a patient. According to some embodiments, a decellularization treatment may render the tissue non-immunogenic. In some cases, a decellularization treatment may at least partially reduce or eliminate immunogenicity in the tissue. Hence, where a matrix material is intended for use in a topical treatment, embodiments may involve at least partially decellularizing the tissue, or processing the tissue without performing a decellularization step. Relatedly, where a matrix material is intended for use in an implantation procedure, embodiments may involve at least partially or fully decellularizing the tissue. In other words, i the intended medical use for the soft tissue matrix composition is that of a temporary covering or product, and not a permanent implantation, the matrix may be suitable for use after being subjected to a partial decellularization regimen or no decellularization regime at all. In some cases, the decellularization techniques can be applied to any of a variety of human and/or heterograft derived matrices.

According to some embodiments, a stromal vascular fraction (SVF) from adipose tissue (see e.g. Gimble et al.; Circulation Research. 2007; 100: 1249-1260, the contents of which are incorporated herein by reference), or other compositions containing progenitor cell populations, stem cell populations, or mixed populations thereof, may be added to the soft tissue matrix. Such fractions or populations may be obtained from cadaveric human tissue or other suitable sources. In some instances, when added to the flowable matrix composition, mesenchymal stem cells may adhere to the flowable matrix substrate. Exemplary techniques for obtaining stromal vascular fractions, progenitor cells, and stem cells from tissue are described in PCT Publication WO 2010/059565 to Shi, the contents of which are incorporated herein by reference.

In some cases, the soft tissue material may be a delaminated dermal tissue. In some cases, the soft tissue material may be a non-delaminated dermal tissue. For example, dermal tissue may have an intact epidermal layer. Alternatively, dermal tissue may be treated to remove the epidermal layer, either partially or completely. Delamination or deepidermization may be accomplished by any of the typical methods known in the field including mechanical debridement of the epidermis by repeated scraping with a sharp instrument such as a surgical scalpel. Alternatively deepidermization may be chemically induced by any of the hypotonic or hypertonic saline methods such as Wilsteed, E M et al.; "*An ultrastructural comparison of dermo-epidermal separation techniques*", J. Cutan. Pathol. 18: 8-12 (1991), the content of which is incorporated herein by reference.

Figure 2:
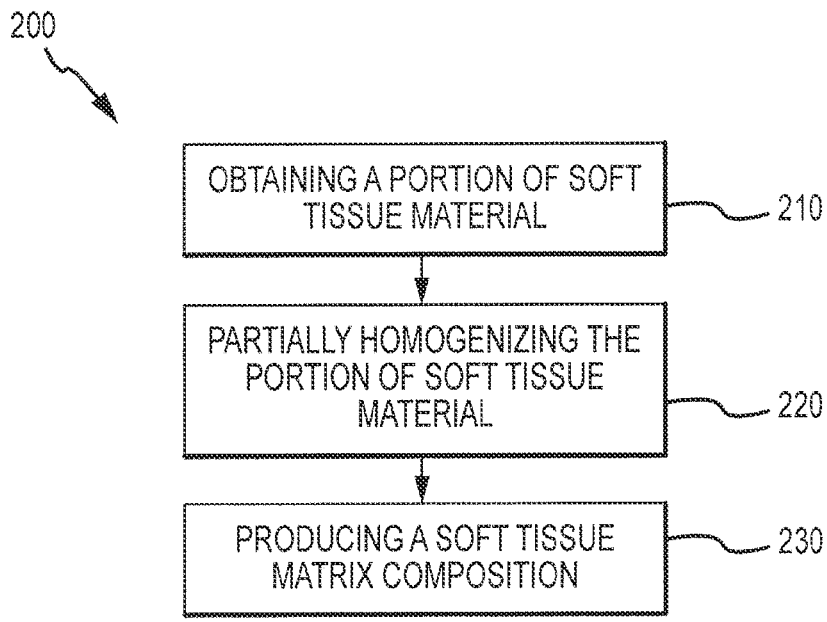
FIG. 2 illustrates aspects of a method for producing a soft tissue matrix composition according to embodiments of the present invention.

According to some embodiments, a soft tissue matrix composition may be produced without treating the source soft tissue material with a cryofracturing protocol. FIG. 2 illustrates aspects of a method 200 for producing a soft tissue matrix composition for use in a patient treatment. As shown here, method 200 includes obtaining a portion of soft tissue material, as depicted by step 210, partially homogenizing the portion of soft tissue material, as depicted by step 220, so as to produce the soft tissue matrix composition, as depicted by step 230.

Figure 3:
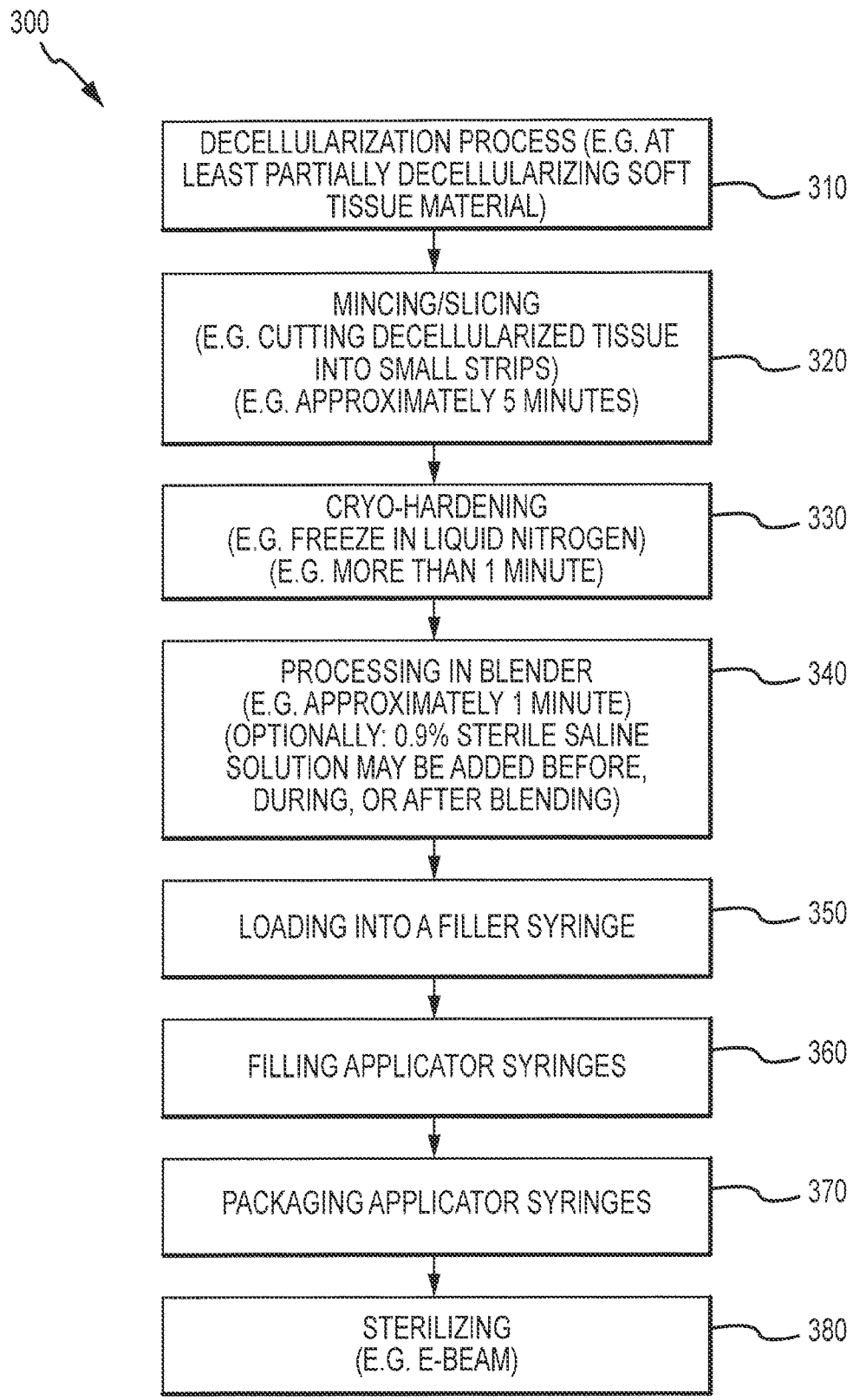
FIG. 3 illustrates aspects of a method for producing a soft tissue matrix composition according to embodiments of the present invention.

FIG. 3 illustrates aspects of matrix composition manufacturing methods, according to embodiments of the present invention. As shown here, manufacturing method 300 may include treating a portion of soft tissue material with a decellularization process, as indicated by step 310. Decellularization may be accomplished by known techniques such as those referenced in Gilbert, T W, Sellaro, T L and Badylak, S F; "*Decellularization of tissues and organs*", Biomaterials, 27, (2006), 3675-3683, the content of which is incorporated herein by reference. Embodiments of the present invention also encompass tissue which is processed according to decellularization techniques such as those described in U.S. Pat. No. 5,336,616, the content of which is incorporated herein by reference. In some cases, the soft tissue material may be completely decellularized. In some cases, the soft tissue materially may be partially decellularized. Optionally, the soft tissue material may not be subjected to a decellularization process. Following the decellularization treatment, the soft tissue material may be cut, minced, or sliced into pieces, as indicated by step 320. For example, a portion of decellularized soft tissue material may be cut or separated into small strips or pieces. Optionally, a wetting agent such as sterile saline can be admixed with the minced pieces, for example after the pieces have been minced in a blender, at which point the tissue material may be the consistency of a putty. In some instances, the cutting process may be performed for about 5 minutes. In some instances, the duration of this time period may vary depending on the type of tissue processed. In some instances, following a decellularization treatment, tissue or material can be processed to remove potentially antigenic cellular debris and proteinaceous materials from the ECM.

Decellularized tissue material can be subjected to a cryo-hardening treatment, as indicated by step 330. For example, the tissue may be immersed in liquid nitrogen, so as to freeze or cryofractured the tissue. In some cases, the soft tissue is treated with liquid nitrogen for a duration of about one minute, or longer. As depicted by step 340, the frozen or cryo-treated soft tissue material may be triturated in a blender. In some instances, the tissue is processed in the blender for a duration of about one minute. In some instances, a wetting agent, or any other additive, may be added to the soft tissue material before, during, or after the trituration process. Exemplary additives may include any of the pharmaceutical excipients that are classified by FDA as generally recognized as safe (GRAS). In some instances, the wetting agent is a 0.9% sterile saline solution. As depicted in step 350, the triturated soft tissue material may then be placed or loaded into a filler syringe. Thereafter, as depicted in step 360, the soft tissue material may be placed or loaded into applicator syringes, for example by extruding the soft tissue material from a filler syringe into an applicator syringe. The loaded applicator syringes can then be packaged, as indicated by step 370. Subsequently, the packaged applicator syringes can be sterilized, for example by exposure to e-beam. According to some embodiments, a 48 cm² amount of decellularized soft tissue may yield approximately 10 c.c. to 15 c.c. of flowable matrix composition, which may in some instances provide enough product to load two or three syringes. The entire process shown in FIG. 3 may take approximately 30 minutes or less, in some instances.

Figure 4:
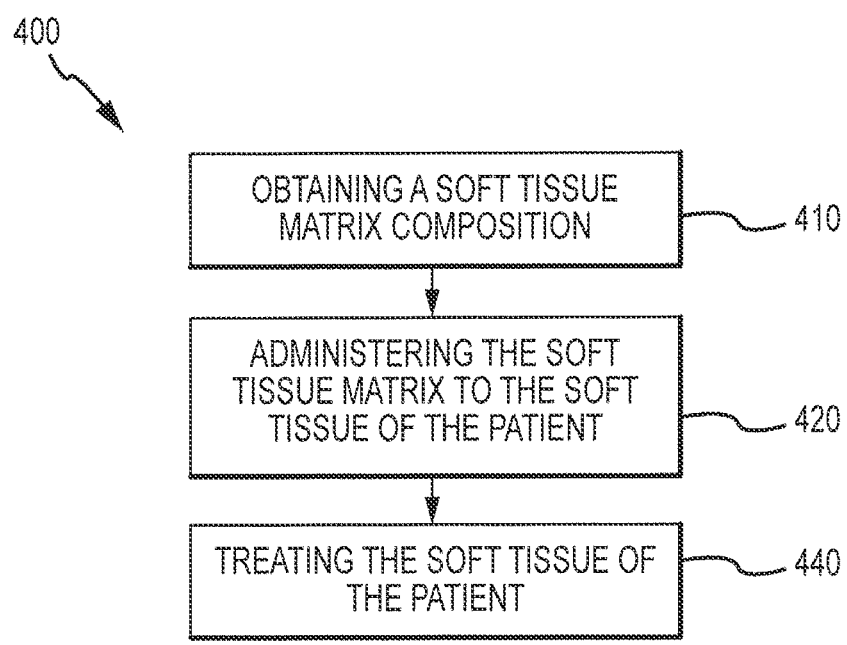
FIG. 4 illustrates aspects of a method for treating a soft tissue of a patient according to embodiments of the present invention.

FIG. 4 illustrates aspects of a therapeutic treatment according to embodiments of the present invention. A method 400 for treating a patient may include obtaining a soft tissue matrix composition, as depicted by step 410, and administering the soft tissue matrix to the soft tissue of the patient, as depicted by step 420, so as to treat the soft tissue of the patient, as depicted by step 430. A patient may be a human or non-human animal. In some cases, the treated soft tissue of the patient referred to in step 430 includes a soft tissue defect. Relatedly, a soft tissue defect may be present in the patient as a skin void, and the administering protocol of step 420 may include at least partially filling the skin void with the soft tissue matrix composition. In some cases, administration step 420 may include delivering the soft tissue matrix with an applicator assembly to the soft tissue. An applicator assembly may include a cannula mechanism, a syringe mechanism, or the like. In some cases, administration step 420 may include manually delivering the soft tissue matrix with a gloved hand. For example, a surgeon may manually administer the soft tissue matrix to the patient tissue or treatment site. According to some embodiments of the present invention, a soft tissue defect may be or include a skin void, a channel wound, an ulcer, a surgical wound, a trauma wound, a chronic wound, an acute wound, an exsanguinating site, or the like. According to some embodiments of the present invention, a soft tissue defect may be or include an ulcer wound, such as a pressure ulcer, a venous ulcer, a diabetic ulcer, or a chronic vascular ulcer. According to some embodiments of the present invention, a soft tissue defect may be or include a surgical wound, such as a general surgery wound, a plastic surgery wound, a reconstructive surgery wound, a urological surgery wound, or a gynecological surgery wound. Some treatment methods may include at least partially covering the matrix, the tissue, or both, with a wound dressing. Some treatment methods may include molding or forming the soft tissue matrix composition into a shape suitable for placement at or within the soft tissue. Such administration techniques can be performed by a surgeon or other suitable medical personnel. In some cases, a soft tissue defect may include an exsanguinating site, and administration of the soft tissue matrix can operate to activate a hemostatic cascade at the exsanguinating site.

According to some embodiments, a flowable acellular human dermal matrix material can be prepared and administered as follows. First, human skin can be recovered in a cutting operation. For example, human full-thickness skin can be severed from a donor, and cut into appropriately sized pieces. The skin can then be processes according to selected delamination, decellularization, or washing steps, or combinations thereof. Subsequently, the skin can be processed according to a cryofracturing procedure, which may involve exposing the skin to liquid nitrogen. Thereafter, the cryofractured skin can be milled or triturated. The resulting putty-like collagen matrix can then be loaded into a syringe for subsequent packaging and sterilization. An exemplary product may be provided as 5 cc syringe loaded with approximately 3 c.c. (or more) of the soft tissue matrix composition. The loaded syringe can be packaged in a TYVEK® peel inner clear plastic tub. This inner tub can be placed in a TYVEK® peel outer tub. The resulting package can be sterilized by e-beam and provided in a double sealed configuration for operating room (OR) use. The flowable matrix product may be indicated for replacement or repair of damaged or inadequate integumental tissue.

Figure 5:
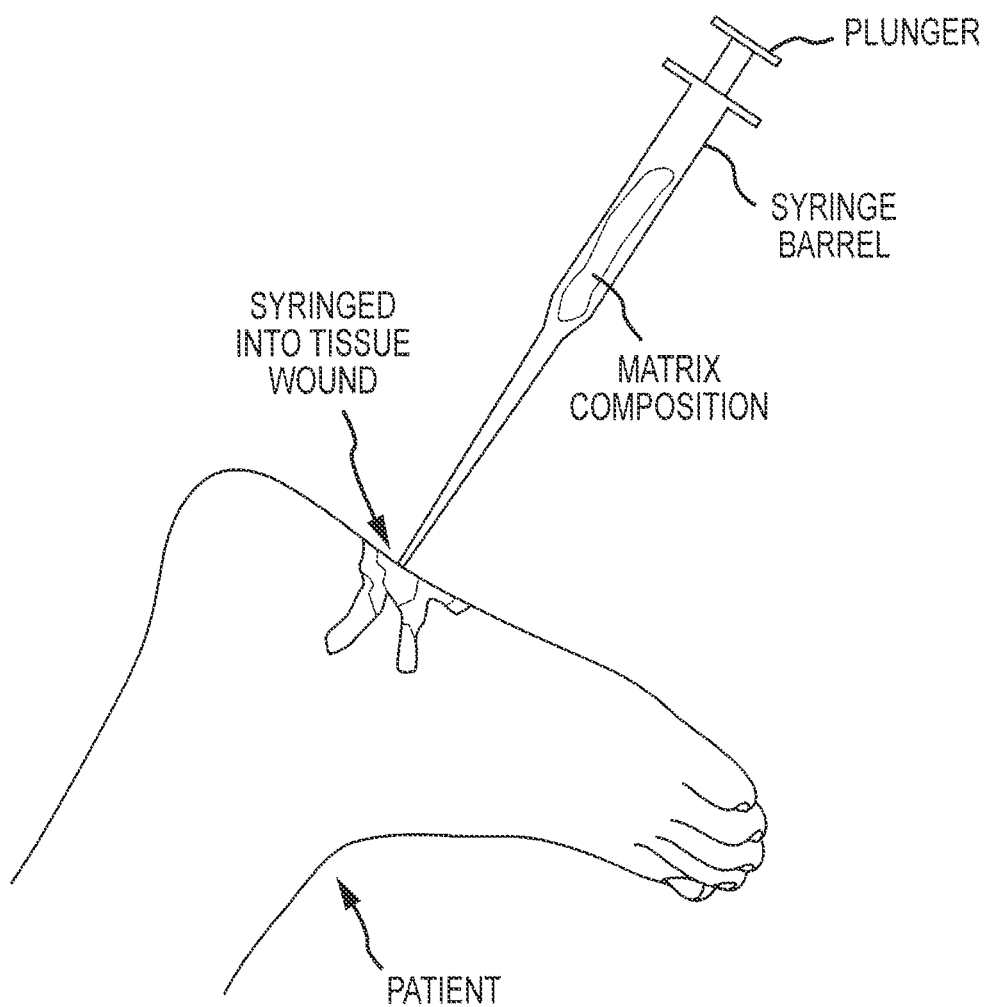
FIG. 5 shows aspects of a process for administering a soft tissue matrix composition to a patient, according to embodiments of the present invention.
Figure 6:
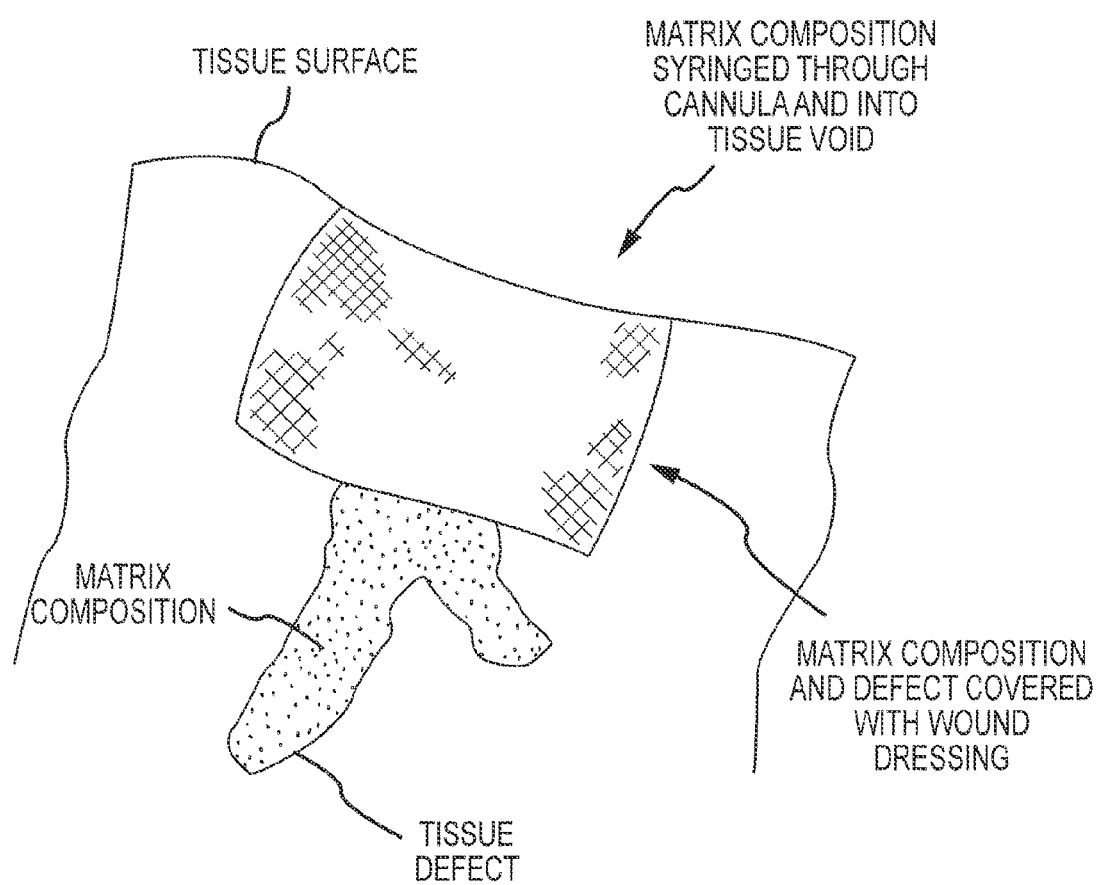
FIG. 6 shows aspects of a process for administering a soft tissue matrix composition to a patient, according to embodiments of the present invention.

As shown in FIG. 5, the flowable matrix composition can be syringed through a cannula into a skin void or tissue wound of a patient. In some embodiments, a tissue treatment product may include a 6 c.c. syringe containing 3 c.c. of flowable matrix composition. In some embodiments, a tissue treatment product may include a 6 c.c. syringe containing 5 c.c. of flowable matrix composition. In use, the flowable matrix composition can be applied to any of a variety of wound types, such as tunneling wounds, channel wounds, invaginated wounds, and the like. According to some embodiments, the matrix composition has a consistency such that it can be delivered or extruded through a standard syringe (e.g. 3 mm orifice) or a cannula, catheter, or similar tube having an inner diameter of less than 4 mm. As shown here, the matrix composition can be delivered from a syringe into a wound bed that has an irregular shape or that is difficult to access. In some embodiments, the matrix composition may be applied manually, for example as a putty. The matrix composition typically does not adhere to surgical glove material. Hence, the flowable product can be easily molded and pressed or formed into patient wounds, without sticking to the surgeon's gloved hand or finger. As shown in FIG. 6, after the matrix composition is syringed through a cannula and into a tissue void, the surgeon or other medical personnel can cover the matrix composition and the patient defect with a wound dressing.

With a flowable matrix composition, embodiments of the present invention provide therapeutic interventions that allow for complete contact of the matrix with an irregular or channeling wound bed. Such materials can be molded or formed, and placed in an irregular wound bed so that sufficient material coats the wound bed to allow for a revascularization and remodeling response to occur. Hence, embodiments provide a suitable matrix for facilitating a healing response. In some instances, matrix compositions of the present invention provide a flowable acellular human dermal matrix, suitable for tissue regeneration indications.

According to some embodiments, soft tissue material can include a structural entity referred to as the extracellular matrix (ECM). The ECM may surround and support cells which are located within the tissue. Often, the ECM may include collagen protein, present in a triple helix fibrillar configuration. Collagen fibers can provide tensile strength and elasticity to the structure of the ECM. During processing procedures as described herein, the macrostructure of the soft tissue, such as the human dermis, can be mechanically disrupted. It has been discovered that although the integrity of the tissue extracellular matrix may be compromised during certain processing procedures (e.g. cryofractured, trituration), the microstructure of the matrix composition can remain intact, or sufficiently intact, for treatment purposes. Relatedly, according to some embodiments, a cryofracturing step can partially disrupt extracellular matrix collagen bundles within the soft tissue material, and a triturating step can further disrupt extracellular matrix collagen bundles within the soft tissue material. Yet, the microfibrillar architecture or structure of the collagen remains sufficiently intact and is available for tissue regeneration. According to some embodiments, the terms microstructure and microarchitecture may be used interchangeably. Hence, the disrupted microstructure of the collagen may also be referred to as a disrupted or disturbed microarchitecture. The microstructure may be measured by histological analysis. For example, tissue material at various stages of the processing (e.g. as shown in FIG. 3), can be histologically stained and microscopically observed. In some instances, the tissue material may be stained with Masson's Trichrome (MT) stain. Such stains can help to visualize the microarchitecture of the collagen bundles that mainly form the extracellular matrix. According to some embodiments, some amount of physical disruption may occur during the deep freeze or cryofractured step, and additional or more pronounced disruption may occur during the trituration/comminution (e.g. blender) steps. The fast freezing of tissue which occurs at liquid nitrogen temperatures may cause interstitial water within the tissue to freeze rapidly. Without being bound by any particular theory, it is thought that rapidly forming ice crystals may exert expanding pressure to somewhat disrupt the microarchitecture. Subsequent exposure to the blender step can further comminute the partially disrupted microarchitecture or microfragments.

Experimental Example 1

A single piece of decellularized human dermal tissue, prior to undergoing a sterilization process, was stored in liquid Nitrogen for a period of time to render the tissue friable. The frozen tissue was milled. The resulting matrix composition, which had the consistency of a putty or paste, was placed into a 5 cc syringe by means of a spatula. The plunger on the syringe was depressed upon the paste to minimize air pockets within the matrix composition. The loaded syringe was placed in a plastic inner tub and heat-sealed with a first TYVEK® cover. This assembly was placed in a larger outer tub, and heat-sealed with a second TYVEK® cover. The entire resulting syringe and package assembly was submitted to approximately 22 kGy electron beam radiation for sterility assurance. Upon subsequent evaluation of the soft tissue matrix composition, it was observed that the matrix composition provided excellent handling and ease of use characteristics.

Experimental Example 2

Six pieces of decellularized (donor derived full-thickness dermal tissue) were obtained (4 cm×8 cm in size). The pieces were each cut into long strips with a knife, and then frozen in liquid nitrogen. The frozen strips were processed in a 200 ml Waring blender. At the onset of blending, loud cracking emanated from the blender. Blending was continued until the loud cracking sounds ceased. 10 g of blended tissue was combined with 1.5 g of 0.9% saline, and the combination was mixed with a spatula, so as to form a matrix composition. The mixed matrix composition was loaded into an irrigation syringe having needle with a 3 mm bore. Upon depression of the syringe plunger, the matrix composition was observed to flow easily through the 3 mm bore needle. Upon additional testing, it was observed that the matrix composition flowed easily through needles having bore sizes of 3 mm and 1.5 mm. However, the matrix composition was not observed to flow easily through an 18 gauge needle. Five samples, each containing approximately 5 ml of matrix composition, were prepared for delivery to an e-beam sterilization facility.

Experimental Example 3

Flow characteristics of skin, tendon, and decellularized dermal matrix materials were evaluated. Samples of each type were prepared, and loaded onto a syringe. The produce was delivered to a luer-loc tipped syringe onto which a luer lock needle could be attached securely. Each sample was loaded along with an amount of 0.9% saline. Each of the three samples were extrudable through a 16 gauge needle, but not a 23 gauge needle. A 1 cc sample of each material was diluted and dissolved in 9 cc of 0.9% saline, respectively. Each of the resulting 10 cc compositions were extrudable through an 18 gauge needle (1.27 mm; 0.050 inches), but not a 23 gauge needle (0.4636 mm; 0.01825 inches). Each of the three sample types were subject to 25-35 kGy E-beam sterilization, and after sterilization the extrudability of the contents in the syringe were compared to a sample that had not been e-beam sterilized. All three sterilized samples showed no difference in the ease of extrusion from the syringe with a 3 mm orifice.

Experimental Example 4

Figure 7:
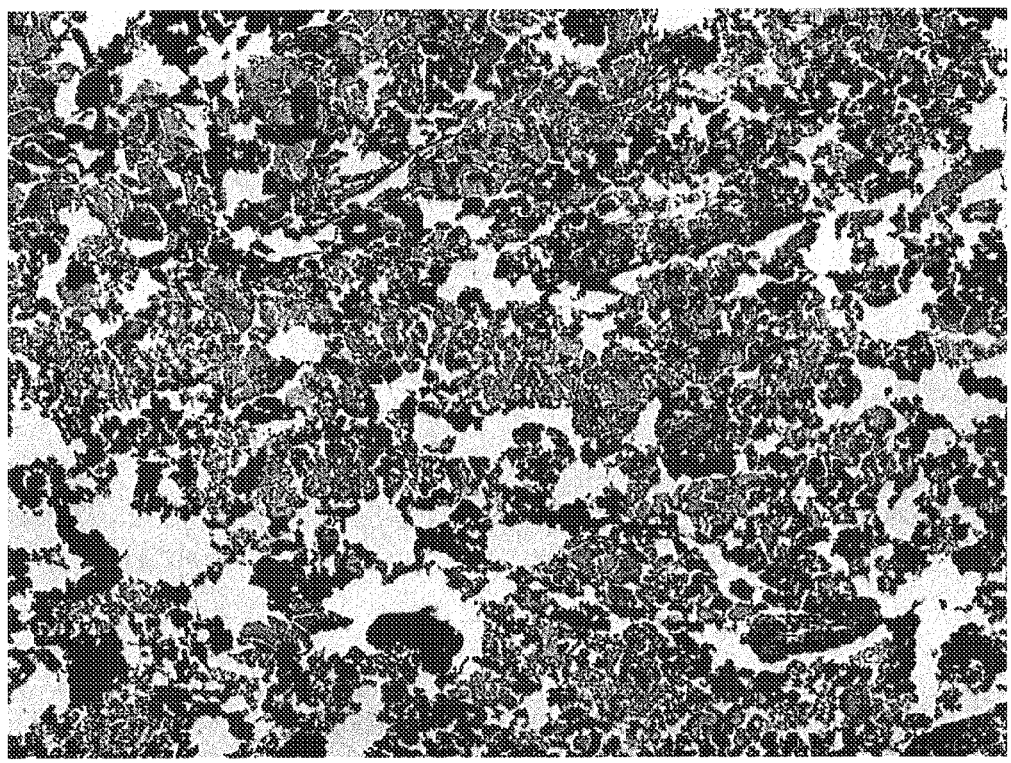
FIG. 7 shows aspects of an exemplary flowable matrix according to embodiments of the present invention.
Figure 8:
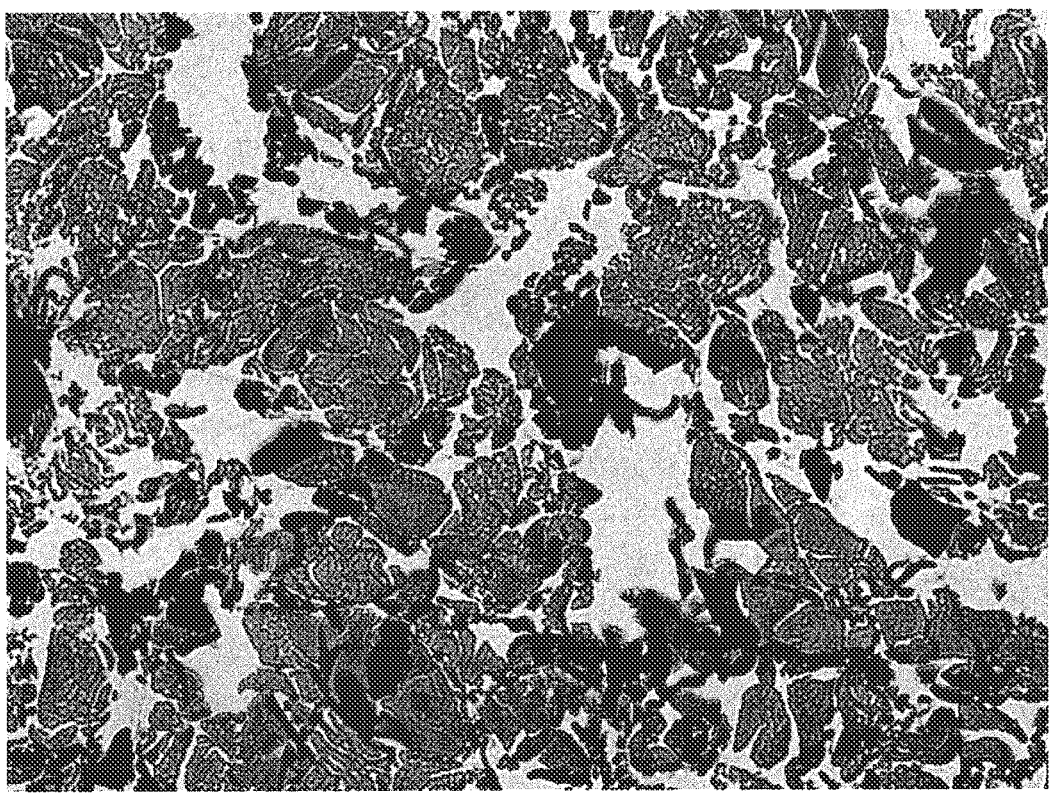
FIG. 8 shows aspects of an exemplary flowable matrix according to embodiments of the present invention.
Figure 9:
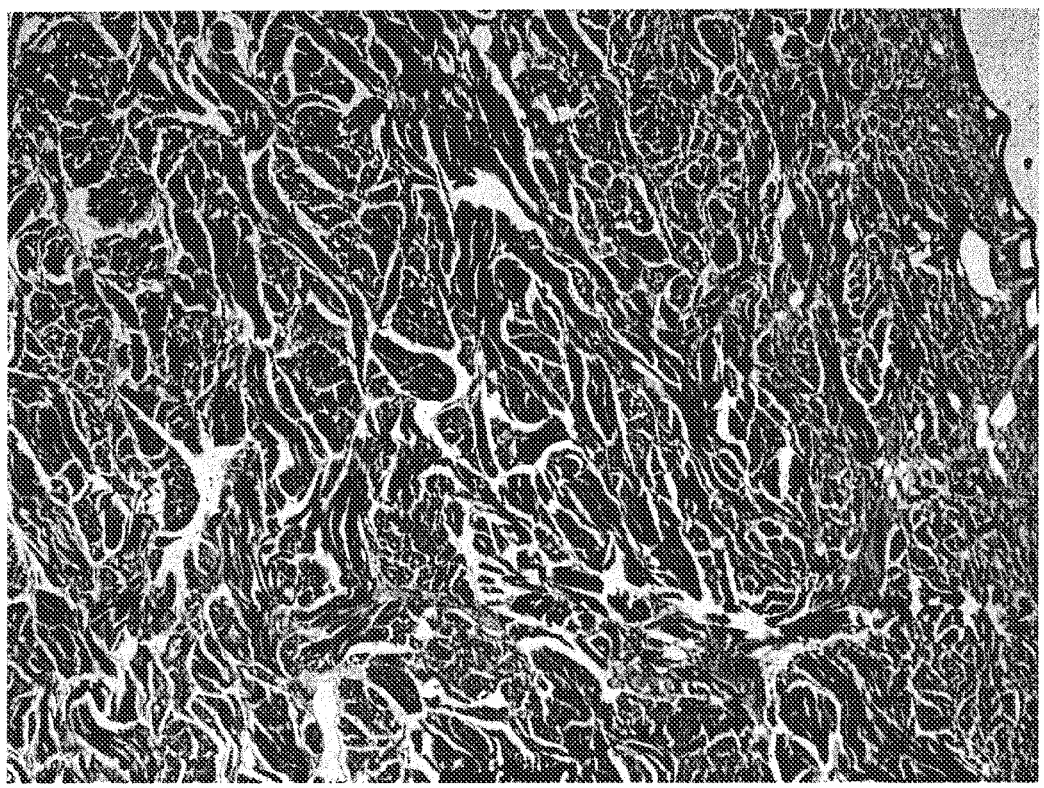
FIG. 9 shows aspects of an exemplary flowable matrix according to embodiments of the present invention.

FIGS. 7 and 8 illustrate 10× and 20× magnifications, respectively, of exemplary flowable matrix embodiments stained with Masson's Trichrome stain. MT stain is often used by histopathologists to visualize connective tissue in a material. Connective tissue of interest in the instant application may primarily be made up of collagen. MT stains collagen various hues of blue. Hence, FIGS. 7 and 8 show a predominantly collagenous matrix derived from a decellularized full thickness human skin source. The collagen matrix in a normal (i.e. non-triturated) extracellular matrix is usually "rope-like" (i.e. a tightly bound fibrous structure). For example, FIG. 9 shows a typical non-cryofractured extracellular matrix structure prior to a trituration step. This Masson's Trichrome stain shows the collagenous microarchitecture as intact as opposed to comminuted. An unexpected and surprising result of a cryofracturing process is the comminuted appearance of the material in FIGS. 7 and 8. More specifically, one would expect a fibrous structure of FIG. 9 to simply be broken, cut, or otherwise reduced into much smaller "ropes" or fibers following trituration. However the material shown in FIGS. 7 and 8 appears to have been comminuted (i.e. pulverized or otherwise reduced to particles). Although a portion of the flowable matrix depicted in FIGS. 7 and 8 has a few identifiable fibers, the majority of it is in a comminuted form.

Delivery and Tendon Embodiments

Tissue is generally not recognized to have the capability to deliver growth factors (GF). GF delivery can be important to retain the GF at the site of repair for sufficient time to allow repair/regeneration. Additionally, the repair process is a temporal process and the addition of GF over time can aid different stages of the repair process. In contrast, a bolus delivery of GF may have a short-term effect or may have no or minimal effect because the GF are rapidly removed from the repair site and cannot influence downstream stages of the repair process.

Platelet rich plasma (PRP) is derived from centrifuging whole blood, has a platelet concentration higher than that of whole blood, is the cellular component of plasma that settles after centrifugation, and contains numerous growth factors (such as vascular endothelial growth factor, transforming growth factor-$\beta 1$, and platelet-derived growth factor-BB). PRP can be used in sports medicine by directly applying the PRP to the injury site. However, there is a lack of evidence showing that PRP can facilitate the repair process. One potential explanation for this is that PRP may not be adequately retained or delivered over the appropriate time frame to permit biological activity. To circumvent this, some practitioners resort to multiple injections, although the obvious downside is multiple patient visits, incurred health care costs and pain/morbidity of the injection site.

Embodiments of the present invention combines the ground tendon as previously described with PRP. Appropriate processing of the ground tendon is beneficial to retain the physical properties of the collagen and extracellular matrix so as to allow slow activation of platelets and the retention of the growth factors that are released from the platelets on the tendon extracellular matrix. These growth factors may interact by hydrophobic, van der walls, ionic, and other means to bind to the ECM.

Controlled delivery of PRP has been previously described using a gelatin carrier (denatured collagen hydrogel). However, ground tendon more closely resembles the intended repair structure and may be preferred. Further, without being bound by any particular theory, it is believed that intact collagen and extracellular matrix can retain the ECM structures better to retain the GF. Exemplary embodiments of the instant invention encompass tendon and PRP compositions that provide for timed and/or controlled release of PRP therefrom, for a variety of tissue repair processes, including cartilage, bone, tendon, and the like.

According to embodiments of the present invention, it is possible to use autologous PRP rather than recombinant growth factors. Additionally, the PRP may be derived from an allogeneic source. In this case the PRP and ground tendon can be combined during the manufacturing process and lyophilized. Lyophilization can control the porosity such as to create a physical barrier to growth factor release. Such porosity could be controlled by methods such as freezing rate, NaCl concentration, and the like. Other allogeneic growth factors can be added to the ground tendon such as BMP-2, -4 and -7 and TGFb-1 extracted from demineralized bone to allow for temporal release of a different set of GF.

There are a number of medical applications. These include the repair of partial tendon tears in which the ground tendon/PRP composite can be delivered to the tear area to facilitate repair. The product composite can also be delivered to facilitate repair of meniscal tears. Typically, the product composite can be delivered to the repair site and the repair can be closed using bioresorbable pins, tacks or sutures. The product composite may also be applied to tendon-bone interface such as for rotator cuff repair. The product composite can be delivered to the interface or footprint area prior to the sutures being pulled tight to position the tendon and bone together with the ground tendon/PRP at the interface. Postoperative rotator cuff tears occur from 11-94% of rotator cuff surgeries. Because of the high retear rate, it is beneficial to explore techniques of biological augmentation of rotator cuff repair. The normal tendon to bone interface includes tendon, non-mineralized fibrocartilage, mineralized fibrocartilage and bone. The normal repair process produces substantial fibrovascular/scar tissue which leads to inferior repair zone and substandard biomechanical strength. Appropriate delivery of the PRP with the appropriate scaffold (ground tendon) can facilitate the appropriate tissue structure.

Hence, embodiments of the present invention encompass compositions and methods that involve flowable/ground tendon (e.g. allograft tissue), optionally for use in delivering drugs, growth factors, and the like.

Bone (or Bone with Mesenchymal Stem Cell) Embodiments

Tissue matrix compositions as disclosed herein, such as soft tissue matrix compositions and the like, may also include bone tissue material, optionally in combination with mesenchymal stem cells. For example, treatment compositions and methods may encompass the use of a flowable decellularized or de-epidermalized skin component (or other soft tissue matrix), in combination with a demineralized bone matrix (DBM) component. A DBM component may include, for example, bone (e.g. allograft) from which inorganic mineral has been removed. In some instances, a DBM component may include an organic collagen matrix material. Relatedly, treatment compositions and methods may encompass the use of a flowable decellularized or de-epidermalized skin component (or other soft tissue matrix), in combination with a material that includes both a bone material component and a mesenchymal stem cell component. For example, a flowable skin or soft tissue matrix material may include an amount of ALLOSTEM® Stem Cell Bone Growth Substitute. Relatedly, a flowable skin or soft tissue matrix material may include an amount of adipose-derived mesenchymal stem cells combined with partially demineralized cancellous bone. In some cases, the bone material and/or mesenchymal stem cells may be present in a morselized form. Hence, compositions and methods as disclosed herein may include a flowable soft tissue or skin matrix material combined with ALLOSTEM® morsels, so as to form a bone putty. Exemplary bone and mesenchymal stem cell compositions and methods for their preparation are described in US 2010/0124776 to Shi, the contents of which are incorporated herein by reference.

According to some embodiments, flowable decellularized skin or de-epidermilized skin (or other soft tissue) can be mixed or combined with DBM morsels or ALLOSTEM® morsels (adipose-derived mesenchymal stem cells combined with partially demineralized cancellous bone) to make a putty formulation with good handling characteristics. For example, such morsels or putty compositions may stay in place upon implantation. Relatedly, such morsels or putty compositions may persist at the site of application (e.g. bony defect area) and resist removal by irrigation and/or contact with blood. In some instances, flowable decellularized skin or de-epidermilized skin (or other soft tissue) can provide an effective carrier to hold DBM and/or mesenchymal stem cells in place and prevent their migration. Such carriers may provide enhanced performance over other carriers such as hyaluronic acid, chitosan, pluronic acid, ceramic cements, carboxymethylcellulose, calcium sulfate, which are typically synthetic, not derived from human tissue, or otherwise do not include flowable decellularized skin or de-epidermilized skin (or other soft tissue). Further, such morsels or putty compositions may remain sufficiently moist or hydrated, such that they are not too dry or crumbly. What is more, such morsels or putty compositions can be terminally sterilized at 15-35 kGy by e-beam for example, without compromising the handling characteristics, such that the putty can be molded into any desired shape, without being or becoming too thin or runny.

While exemplary embodiments have been described in some detail, by way of example and for clarity of understanding, those of skill in the art will recognize that a variety of modification, adaptations, and changes may be employed. Hence, the scope of the present invention should be limited solely by the claims.

What is claimed is:

1. A soft tissue matrix composition for use in a patient treatment, the composition consisting of: a cryofractured human soft tissue material having a mechanically disrupted extracellular matrix collagen or macrostructure and a partially disrupted collagen microfibrillar architecture, wherein the cryofractured tissue material is in a hydrated state, the hydration comprising the natural interstitial water of the cryofractured soft tissue material that is present prior to cryofractionation; and a wetting agent, wherein the wetting agent is at least one wetting agent selected from the group consisting of water, saline solution, phosphate buffered saline (PBS), sodium dodecyl sulfate, sodium stearate, benzalkonium chloride, 3-[(3-cholamidopropyl)dimethylammonio]-1-propanesulfonate (CHAPS), lecithin, (p-t-Octylphenoxy)polyethoxyethanol, and nonoxynol-9.

2. The soft tissue matrix composition according to claim 1, wherein the soft tissue matrix composition is present in an applicator assembly.

3. The soft tissue matrix composition according to claim 1, wherein the human soft tissue material is acellular.

4. The soft tissue matrix composition according to claim 1, wherein the human soft tissue material is at least partially decellularized.

5. The soft tissue matrix composition according to claim 1, wherein the human soft tissue material is not partially or completely decellularized.

6. The soft tissue matrix composition according to claim 1, wherein the soft tissue matrix composition does not adhere to a surgical glove material.

7. The soft tissue matrix composition according to claim 1, wherein the soft tissue matrix composition does not adhere to a material selected from the group consisting of latex, neoprene, vinyl, and nitrile.

8. The soft tissue matrix composition according to claim 1, wherein the soft tissue matrix composition has a putty consistency.

9. The soft tissue matrix composition according to claim 1, wherein the soft tissue matrix composition has a shear resistance of 250-2,500 Pascal seconds at room temperature.

10. The soft tissue matrix composition according to claim 1, wherein the soft tissue matrix composition has a shear resistance of 1,000-2,000 Pascal seconds at room temperature.

11. The soft tissue matrix composition according to claim 1, wherein the soft tissue matrix composition can pass through a bore hole of a 18 g needle and not through a bore hole of a 26 g needle.

12. The soft tissue matrix composition according to claim 1, wherein the cryofractured tissue material is in a naturally hydrated state.

13. The soft tissue matrix composition according to claim 1, wherein the cryofractured tissue material is in a partially hydrated state.

14. The soft tissue matrix composition according to claim 1, wherein the wetting agent is water.

15. The soft tissue matrix composition according to claim 1, wherein the wetting agent is a saline solution.

16. The soft tissue matrix composition according to claim 1, wherein the wetting agent is a 0.9% sterile saline solution.

17. The soft tissue matrix composition according to claim 1, wherein the wetting agent is phosphate buffered saline (PBS).

18. The soft tissue matrix composition according to claim 1, wherein the wetting agent is sodium dodecyl sulfate.

19. The soft tissue matrix composition according to claim 1, wherein the wetting agent is sodium stearate.

20. The soft tissue matrix composition according to claim 1, wherein the wetting agent is benzalkonium chloride.

21. The soft tissue matrix composition according to claim 1, wherein the wetting agent is 3-[(3-cholamidopropyl) dimetylammonio]-1-propanesulfonate (CHAPS).

22. The soft tissue matrix composition according to claim 1, wherein the wetting agent is lecithin.

23. The soft tissue matrix composition according to claim 1, wherein the wetting agent is (p-t-Octylphenoxy)polyethoxyethanol.

24. The soft tissue matrix composition according to claim 1, wherein the wetting agent is nonoxynol-9.

25. The soft tissue matrix composition according to claim 1, wherein at least a portion of the human soft tissue material is in minced or sliced pieces.

26. The soft tissue matrix composition according to claim 1, wherein at least a portion of the soft tissue matrix composition is in comminuted form.

27. The soft tissue matrix composition according to claim 1, wherein the human soft tissue material is selected from the group consisting of amnion tissue, umbilical cord tissue, chorionic tissue, intestine tissue, tendon tissue, and skin tissue.

28. The soft tissue matrix composition according to claim 1, wherein the human soft tissue material is skin.

29. The soft tissue matrix composition according to claim 1, wherein the human soft tissue material is full thickness skin or skin lacking the epidermal layer.

30. The soft tissue matrix composition according to claim 1, wherein the human soft tissue material is amnion tissue.

31. The soft tissue matrix composition according to claim 1, wherein the human soft tissue material is umbilical cord tissue.

32. The soft tissue matrix composition according to claim 1, wherein the human soft tissue material is chorionic tissue.

33. The soft tissue matrix composition according to claim 1, wherein the human soft tissue material is intestine tissue.

34. The soft tissue matrix composition according to claim 1, wherein the human soft tissue material is tendon tissue.

35. A soft tissue matrix composition for use in a patient treatment, the composition consisting of: a cryofractured and triturated human soft tissue material having a mechanically disrupted extracellular matrix collagen or macrostructure and a partially disrupted collagen microfibrillar architecture, wherein the cryofractured and triturated tissue material is in a hydrated state, the hydration comprising the natural interstitial water of the cryofractured and triturated human soft tissue material that is present prior to cryofractionation and trituration; and a wetting agent, wherein the wetting agent is at least one wetting agent selected from the group consisting of water, saline solution, phosphate buffered saline (PBS), sodium dodecyl sulfate, sodium stearate, benzalkonium chloride, 3-[(3-cholamidopropyl)dimetylammonio]-1-propanesulfonate (CHAPS), lecithin, (n-t-Octylphenoxy)polyethoxyethanol, and nonoxynol-9.

36. The soft tissue matrix composition according to claim 35, wherein the soft tissue matrix composition is present in an applicator assembly.

37. The soft tissue matrix composition according to claim 35, wherein the human soft tissue material is acellular.

38. The soft tissue matrix composition according to claim 35, wherein the human soft tissue material is at least partially decellularized.

39. The soft tissue matrix composition according to claim 35, wherein the human soft tissue material is not partially or completely decellularized.

40. The soft tissue matrix composition according to claim 35, wherein the soft tissue matrix composition does not adhere to a surgical glove material.

41. The soft tissue matrix composition according to claim 35, wherein the soft tissue matrix composition does not adhere to a material selected from the group consisting of latex, neoprene, vinyl, and nitrile.

42. The soft tissue matrix composition according to claim 35, wherein the soft tissue matrix composition has a putty consistency.

43. The soft tissue matrix composition according to claim 35, wherein the soft tissue matrix composition has a shear resistance of 250-2,500 Pascal seconds at room temperature.

44. The soft tissue matrix composition according to claim 35, wherein the soft tissue matrix composition has a shear resistance of 1,000-2,000 Pascal seconds at room temperature.

45. The soft tissue matrix composition according to claim 35, wherein the soft tissue matrix composition can pass through a bore hole of a 18 g needle and not through a bore hole of a 26 g needle.

46. The soft tissue matrix composition according to claim 35, wherein the cryofractured tissue material is in a naturally hydrated state.

47. The soft tissue matrix composition according to claim 35, wherein the cryofractured tissue material is in a partially hydrated state.

48. The soft tissue matrix composition according to claim 35, wherein the wetting agent is water.

49. The soft tissue matrix composition according to claim 35, wherein the wetting agent is a saline solution.

50. The soft tissue matrix composition according to claim 35, wherein the wetting agent is a 0.9% sterile saline solution.

51. The soft tissue matrix composition according to claim 35, wherein the wetting agent is phosphate buffered saline (PBS).

52. The soft tissue matrix composition according to claim 35, wherein the wetting agent is sodium dodecyl sulfate.

53. The soft tissue matrix composition according to claim 35, wherein the wetting agent is sodium stearate.

54. The soft tissue matrix composition according to claim 35, wherein the wetting agent is benzalkonium chloride.

55. The soft tissue matrix composition according to claim 35, wherein the wetting agent is 3-[(3-cholamidopropyl)dimetylammonio]-1-propanesulfonate (CHAPS).

56. The soft tissue matrix composition according to claim 35, wherein the wetting agent is lecithin.

57. The soft tissue matrix composition according to claim 35, wherein the wetting agent is (p-t-Octylphenoxy)polyethoxyethanol.

58. The soft tissue matrix composition according to claim 35, wherein the wetting agent is nonoxynol-9.

59. The soft tissue matrix composition according to claim 35, wherein at least a portion of the human soft tissue material is in minced or sliced pieces.

60. The soft tissue matrix composition according to claim 35, wherein at least a portion of the soft tissue matrix composition is in comminuted form.

61. The soft tissue matrix composition according to claim 35, wherein the human soft tissue material is selected from the group consisting of amnion tissue, umbilical cord tissue, chorionic tissue, intestine tissue, tendon tissue, and skin tissue.

62. The soft tissue matrix composition according to claim 35, wherein the human soft tissue material is skin.

63. The soft tissue matrix composition according to claim 35, wherein the human soft tissue material is full thickness skin or skin lacking the epidermal layer.

64. The soft tissue matrix composition according to claim 35, wherein the human soft tissue material is amnion tissue.

65. The soft tissue matrix composition according to claim 35, wherein the human soft tissue material is umbilical cord tissue.

66. The soft tissue matrix composition according to claim 35, wherein the human soft tissue material is chorionic tissue.

67. The soft tissue matrix composition according to claim 35, wherein the human soft tissue material is intestine tissue.

68. The soft tissue matrix composition according to claim 35, wherein the human soft tissue material is tendon tissue.

* * * * *

UNITED STATES PATENT AND TRADEMARK OFFICE
CERTIFICATE OF CORRECTION

PATENT NO.        : 9,744,266 B2
APPLICATION NO.   : 14/858295
DATED             : August 29, 2017
INVENTOR(S)       : Reginald L. Stilwell et al.

It is certified that error appears in the above-identified patent and that said Letters Patent is hereby corrected as shown below:

In the Claims

Claim 35, Column 19, Line 3: replace "n-t-Octylphenoxy" with -- p-t-Octylphenoxy --

Signed and Sealed this
First Day of May, 2018

Andrei Iancu
*Director of the United States Patent and Trademark Office*